United States Patent
Xinxian

(12) 
(10) Patent No.: US 6,290,995 B1
(45) Date of Patent: Sep. 18, 2001

(54) PLANT DRUG FOR PREVENTING CANCER II

(76) Inventor: Zhao Xinxian, 67-08 168th St., Flushing, NY (US) 11365

( * ) Notice: Subject to any disclaimer, the term of this patent is extended or adjusted under 35 U.S.C. 154(b) by 0 days.

(21) Appl. No.: 09/500,056

(22) Filed: Feb. 8, 2000

(51) Int. Cl.$^7$ ................................................. A61K 35/78
(52) U.S. Cl. ............................................................ 424/773
(58) Field of Search ................................ 424/195.1, 773

(56) References Cited

U.S. PATENT DOCUMENTS

| | | | |
|---|---|---|---|
| 5,443,839 | * | 8/1995 | Meybeck .............................. 424/450 |
| 5,447,719 | * | 9/1995 | Kamataki .......................... 424/195.1 |
| 5,643,598 | * | 7/1997 | Meybeck .............................. 424/450 |
| 6,083,921 | * | 7/2000 | Xu ..................................... 424/195.1 |

OTHER PUBLICATIONS

Computer West JPAB Abstract JP360274 35 Tsuboi et al "Extracting Method for Extract with High Baicalein Content", Feb. 8, 1988.*

Computer West JPAB Abstract JP361050921"Purification of Baicalin", Mar. 1986.*

Computer West JPAB Abstract JP36105918 "Liquid Composition Containning Baicalin or Baicalein and External Drug for Skin or Skin Cosmetic Containing Same", Jan. 1986.*

Computer West DWPI Abstract 1994–034629 EP642793 Fukuda et al "Apoptosis–Inducing Compsn Containing Baicalin or Baicalein–Induces Apopptosis in Cancer and Virally Infected Cells" Mar. 29, 1995.*

Computer West DWPI Abstract 1988–073860 JP63027435 "Extracting Extract Contg. High Baicalein Content by Adding Water to Powder of Scutellaria Root and Standing at Elevated Temp., Before EXTN., Used to Treat ECzema and Dermatitis", Feb. 1988.*

Computer West DWPI Abstract 1984–007494 "Plant Extract Prepn Effective for Treating Arteriosclerosis, Apoplexy, Encephalomalcia and Hypdercholesterolaemia", Feb. 1988.*

* cited by examiner

*Primary Examiner*—Herbert J. Lilling

(57) ABSTRACT

This invention relates to new safe natural drug, which is prevention of cancer and control of cancer cells. Specifically, this invention provides methods for producing of Berberine and Baicalin.

Also, the present invention proved a new radioimmunoassay (RIA) method for precise determination of Berberine and Baicalin. The RIA is an efficient analytical method for large clinical programs including double blind analysis (DBA), and good clinical practice (GCP).

1 Claim, No Drawings

PLANT DRUG FOR PREVENTING CANCER II

BACKGROUND OF THE INVENTION

This invention relates to new safe natural drug, which is prevention of cancer and control of cancer cells. Specifically, this invention provides methods for producing of Berberine and Baicalin.

Also, the present invention proved a new radioimmunoassay (RIA) method for precise determination of Berberine and Baicalin. The RIA is an efficient analytical method for large clinical programs including double blind analysis (DBA), and good clinical practice (GCP).

DESCRIPTION OF PRIOR ART

Cancer is the second leading cause of death in the United States, and the incidence of cancer continues to climb annually. In recent years, about 1 million new cases of cancer are diagnosed yearly in the U.S. About half million people and 7 million people of annual deaths in the U.S. and in the world, respectively.

Many reports indicated that the side effects of plant's anti cancer drugs are lower than chemical and antibiotic's anti cancer drugs, Therefore, the development of plant drug has progressed very fast now. Taxol, for example, is a novel anti cancer plant drug isolated from the needles and bark of the western yew, Taxus brevifolia. It is the prototype for a new class of antitumor drugs, which are characterized by their capacity to promote the assembly of microtubules. Clinical trials conducted in the late 1980s and early 1990s demonstrated impressive clinical activities against advanced ovarian and breast cancer.

However, taxol has two big problems. The first problem is that natural source of taxol is very limited. And the second problem is that taxol is a poor-water soluble. Vehicles for parental administration on taxol cause serious side effects.

The most remarkable progress in the last 25 years has been in cancer biology. Now we understand what is required to turn a normal cell into a cancer cell. Cancer arises when a single cell changes so that it divides continuously, released from the controls that constrain the replication of normal cells. This transformation is due to changes in the function and activity of genes, which are segments of DNA. Of the 100,000 genes found in the human genome, only the altered activities of a small number of genes are responsible for transforming a normal cell into a cancer cell. These genes normally function to instruct cells to produce accelerators that drive cells to proliferate, brakes that control proliferation, or the repair of DNA damage or the elimination of damaged cells.

We now know that DNA changes are the fundamental cause of all cancers. These changes can occur due to chemicals, viruses, radiation and mistakes of duplicating DNA. When a normal cell recognizes damage to its DNA, it stops the process of growth and division. In the development of cancer, checkpoint controls are lost and the cell continues to divide, transmitting its damaged DNA to new cells.

Cancer does not develop at short time. The molecular changes necessary to transform a normal cell into a cancer cell may take years to accumulate. This is one reason for prevention of cancer by administering drugs that inhibit the crucial molecular events causing transformation.

The present invention disclosed that control process of turning a normal cell into a cancer cell by special natural and safe drugs. Recently a number of gene expression systems have been developed that can be regulated by the administration of specific small molecule drugs. It is important that the small molecule drugs are easily administered. Some of the earliest systems include exposure to heavy metal, and steroid hormones, but they are not suited for in vivo human. These systems, however, are suitable to study for the effect of small molecular drugs on controllable oncogenes, and to study for the treatment of cancer.

So far, no one drug has been succeeded to treat or prevent cancer by control cancer cells and without adverse side effects.

SUMMARY OF THE INVENTION

A new safe pharmaceutical composition in accordance with the present invention for prevention cancer and control cancer cells comprises Berberine and Baicalin.

Methods of control cancer cells include inhibiting oncogenes, increasing activity of tumor suppressor, inhibiting cancer cells proliferation, inhibiting growth of transplanted cancer, inhibiting cancer incidence.

Also, the present invention proved a new radioimmunoassay (RIA) method for precise determination of Berberine and Baicalin. The RIA is an efficient analytical method for large clinical programs including double blind analysis (DBA), and good clinical practice (GCP).

DETAILED DESCRIPTION OF THE INVENTION

Recent developments in cancer research, more specifically, in molecular biology, biochemical aspects, indicated that controlling cancer cells is more important. For example, control oncogene expression, apoptosis, and differentiation of cancer cells are several key steps in process of control cancer. The control of oncogene expression, apoptosis and differentiation of cancer is focus in cancer biology and molecular pharmacology of anticancer drug. For example, concentration of oncogene c-myc and c-myb RNA is rapid increased in human leukemia and other cancer cell, and a rapid decline in the expression of c-myc and c-myb RNA was seen in cancer cells induced to differentiate. Control oncogene expression, apoptosis and differentiation of cancer cells can control and preventing carcinogenesis.

The compositions of drugs and the sources of its components are listed as below.

TABLE 1

| Component | Source |
|---|---|
| Berberine (BE) | Berberis poiretii Schined |
| | Berberis julianae Schneid |
| | Berberis soulieana Schined |
| | Berberis wilsonae Schined |
| Baicalin (BA) | Scutellaria baicalensis Georgi |
| | Scutellaria scordifolia Fisch |

TABLE 2

| Component | Weight percent | Preferred composition weight percent |
|---|---|---|
| BE | 30–70 | 50 |
| BA | 30–70 | 50 |

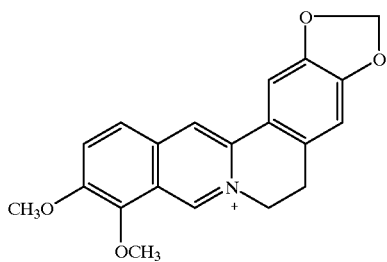

Berberine

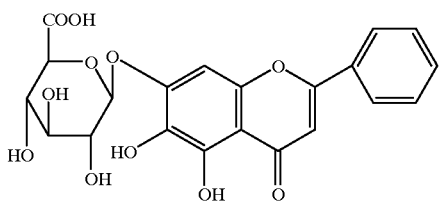

Baicalin

The following specific examples will provide detailed illustrations of methods of producing relative drugs, according to the present invention and pharmaceutical dosage units containing relative drugs. Moreover, examples described pharmaceutical characters of drugs, which demonstrates its effectiveness in control of cancer cells. These examples are not intended, however, to limit or restrict the scope of the invention in any way, and should not be construed as providing conditions, parameters, reagents, or starting materials which must be utilized exclusively in order to practice the present invention.

EXAMPLE 1

Extraction of Berberine

Berberine was extracted from Berberis poivetii Schined or Berberrros julianae Schined. The roots of plant dried and powdered. 3 liters of 0.1% $H_2SO_4$ was added to 1 kg of dried powder and allowed to stand for one day at room temperature. The solution was filtered and extracted filtrate saved. 2000 ml of 0.1% $H_2SO_4$ added to the residue, and extracted was repeated. The filtrate combined. HCl added to filtrate and adjusted to pH 1.5. NaCl added the solution of HCl and adjusted concentration of NaCl to 10% with stir. And allowed to stand for two days at room temperature. The solution was filtered and the residue was saved. The hot water (60° C.) added to the residue and suspension obtained. $Ca(OH)_2$ was added to suspension and adjusted pH to 8.5. Solution of $Ca(OH)_2$ was filtered and filtrate saved. HCl added to filtrate and adjusted pH to 1.5 and allowed for standing 2 hours at room temperature. Precipitate was obtained. Precipitate was filtered and the residue saved. Residue was washed by distilled water. Dried under vacuum. Powdered. The final product is Berberine.

EXAMPLE 2

Extraction of Baicalin

Baicalin was extracted from the roots of Scutellaria baicalensis George. The roots of plant dried and powdered. 10 liters water (80° C.) was added to 1 kg of dried powder and allowed standing a half of hour. The extraction was repeated twice by collecting the hot water, replacing it with an equal volume of water (80° C.). The water was combined. HCl added to water and adjusted pH to 1.5 and allowed standing for a half of hour at 80° C. The solution filtered and residue saved. The residue washed by 95% ethanol. The residue filtered under vacuum. Water added to residue and adjusted pH to 6.8 by 40% NaOH. Active carbon added to water solution of NaOH and allowed standing for a half of hour at 80° C., then allowed standing for 10 hours at room temperature. The precipitant filtered under vacuum. The precipitant was washed by 95% ethanol and dried at 60° C.

EXAMPLE 3

Radioimmunoassay for the Quantitative Determination of Berberine

A radioimmunoassay for the determination of the pilogram ($10^{-12}$ g) amounts of Berberine has been developed. The measuring range of the assay extends from 0.05 to 20 ng of Berberine. This assay allows the rapid, sensitive and precise determination of Berberine. Berberine is currently being determined by a number of methods including thin-layer chromatography. The sensitivity of thin-layer methods is in the microgram range. Also only a few of samples can be analyzed per day. In the past years, the radioimmunoassay (RIA) has proven to be very useful for the determination of various plant constituents. This method, using the sensitivity and selectivity of high-affinity antibodies together with tracer antigens of very high specific activity, allows the precise measurement of very low concentrations of compounds in manufacture process, crude plant extracts and in blood of patients who treated with Berberine. More important, the RIA method is allowed the analysis of up to more than five hundreds per day. Therefore, RIA is an efficient analytical method for large clinical programs, including double blind analysis (DBA) and good clinical practice (GLP). GLP and DBA are requested by FDA for approval a new drug. The present invention disclosed that in a high specific RIA of Berberine, which allows the precise quantification of Berberine in the pilogram ($10^{-12}$ g) range. Method: $^3$H-Berberine was synthesized. Berberine (1 g) and hemisuccinate (1 g) were dissolved in 2.5 ml pyridine and the solution was refluxed for 1 hour. The solution was diluted with 7.5 ml $H_2O$ and the pH was adjusted to 4 by IN HCl. The solution was extracted 10 ml $CHCl_3$ with three times. The $CHCl_3$-phases were pooled and concentrated to 1 ml under vacuum. The concentrate mixed with 2 ml petrol ether (40°–60° C.). The precipitate was separated by filtration and recrystallized from MeOH yielding Berberine hemisuccinate. 50 mg Berberine hemisuccinate dissolved in 5 ml of 50% of aqueous $C_5H_5N$. Added 50 mg of 1-ethyl-3-(3-dimethylaminopropyl)-carbodiimide hydrochloride in 50% aqueous $C5H_5N$ with stirring at room temperature. 82 mg of solution of bovine serum albumin (BSA) was added to aqueous $C_5H_5N$ and then mixture was stirred for 24 hours at room temperature. The mixture dialysed against $H_2O$ for 4 days, and Berberine hemisuccinate conjugate.

The conjugate was administrated to rabbits. After 4 weekly intradermal immunizations, intramuscular booster injections were given monthly. The blood was collected 1 and 2 weeks after each booster. The whole cells were removed by centrifugation. The antiserum was collected and stored at –20° C. Samples and standards were added to glass tubes. ³H-Berberine (5000 cpm in 0.1 ml) and H₂O were added to tubes. Incubation was started by addition of antiserum. The samples and standards were incubated for 1 hour at room temperature following by the addition of 1 ml of 98% solution of freshly prepared $(NH_4)_2SO_4$ and mixing. The samples and standards were further incubated for 1 hour at 20° C. and then centrifuged (10 min at 4000 rpm). The pelles were washed with 50% of $(NH_4)_2SO_4$ then dissolved in 0.25 ml of H₂O and mixed with 1 ml of scintillation. The tubes were counted for radioactivity. The results RIA-calculations were done on a corrected count by linear interpolation from the standard curve, after correction for dilution.

EXAMPLE 4

Radioimmunoassay for the Quantitative Determination of Baicalin Method: ³H-Baicalin was synthesized. Baicalin (1 g) and hemisuccinate (1 g) were dissolved in 2.5 ml pyridine and the solution was refluxed for 1 hour. The solution was diluted with 7.5 ml H₂O and the pH was adjusted to 4 by IN HCl. The solution was extracted 10 ml $CHCl_3$ with three times. The $CHCl_3$-phases were pooled and concentrated to 1 ml under vacuum. The concentrate mixed with 2 ml petrol ether (40°–60° C). The precipitate was separated by filtration and recrystallized from MeOH yielding Baicalin hemisuccinate. 50 mg Baicalin hemisuccinate dissolved in 5 ml of 50% of aqueous $C_5H_5N$. Added 50 mg of 1-ethyl-3-(3-dimethylaminopropyl)-carbodiimide hydrochloride in 50% aqueous $C_5H_5N$ with stirring at room temperature. 82 mg of solution of bovine serum albumin (BSA) was added to aqueous $C_5H_5N$ and then mixture was stirred for 24 hours at room temperature. The mixture dialysed against H₂O for 4 days, and Baicalin hemisuccinate conjugate. The conjugate was administered to rabbits. After 4 weekly intradermal immunizations, intramuscular booster injections were given monthly. The blood was collected 1 and 2 weeks after each booster. The blood were removed whole cells by centrifugation. The antiserum was collected and stored at −20° C. Samples and standards were added to glass tubes. ³H-Baicalin (5000 cpm in 0.1 ml) and H₂O were added. Incubation was started by addition of antiserum. The samples and standards were incubated for 1 hour at room temperature following by the addition of 1 ml of 98% solution of freshly prepared $(NH_4)_2SO_4$ and mixing. The samples and standards were further incubated for 1 hour at 20° C. and then centrifuged (10 min at 4000 rpm). The pelles were washed with 50% of $(NH_4)_2SO_4$ then dissolved in 0.25 ml of H₂O and mixed with 1 ml of scintillation. The tubes were counted for radioactivity. The results RIA-calculations were done on a corrected count by linear interpolation from the standard curve, after correction for dilution.

EXAMPLE 5

The Effect of Drug on Prevention of Epidermis Cancer

It is known that tetradecanoyphorbol-13-acetate (TPA) is strong tumor promoter and TPA can remarkable increase [³H] thymidine incorporation in mouse epidermis and then to induce Epidermis cancer.

Method: Mice were treated with TPA and the rate of [³H] thymidine incorporation was determined 20 hours later. Male mice (7–9 weeks old) used for experiments. Only mice showing no hair regrowth following shaving were used. Animals were injected intraperitoneally (i.p.) with TPA or 95% saline. After 20 hours, mice were injected i.p. with 60 μCi of [³H] thymidine (2 Ci/mmol) 20 minutes before sacrifice. Epidermal scrapings were prepared. Homogenized in distilled water at 4° C., and the macromolecules precipitated with 0.4 N trichloracetic acid (TCA). Following 6 washes with 0.2 N TCA at 4° C. and 2 washes with absolute ethanol at room temperature, the nucleic acids were hydrolyzed with 0.5 N TCA at 90° C. for 5 minutes. The hydrolysates (0.2 ml aliquots) were counted in a scintillation counter and assayed for DNA. Each value is the mean± range for three separately treated mice. Each counted aliquot (0.2 ml) contained approximately 10 μg of DNA.

TABLE 3

Effect of Drug on the rate of [³H] thymidine incorporation in normal and TPA-stimulated mouse epidermis

| Treatment | Dose (mg/kg. i.p.) | Specific activity (cpm/μg DNA) | |
| --- | --- | --- | --- |
| | | Normal | TPA |
| Saline | — | 40.0 ± 0.8 | 120 ± 4.5 |
| Drug 1 | 10.0 | 30.5 ± 0.7 | 31 ± 4.3 |
| Drug 2 | 1.0 | 36.5 ± 0.7 | 69 ± 2.3 |

Data of table 3 indicated that Drug can remarkable inhibit DNA synthesis of TPA-stimulated mouse epidermis. Therefore, the experiments indicated that Drug can prevent epidermis cancer.

EXAMPLE 6

Effect of Drug on Tumor Suppressor of Gastric Cancer Cells

Gastric cancer is one of the most cancer diseases in the world. The recent progress made in molecular genetics has revealed that p53 gene is a tumor suppressor gene. Disorder of mutations of p53 plays a very important role in the development of many cancers. D17S5 hypermethylation, 17p allelic and p53 mutations appears to be the most common genetic abnormalities in cancer including in the development of gastric cancer. However, determinate tumor suppressor of gastric cancer cells is very difficult and experimental errors are lager. The present invention proved a new and easy method for determinate tumor suppressor of gastric cancer cells.

Methods:

The gastric cancer cells and normal cells were cultured in RPMI 1640 medium supplement with 10% fetal bovine serum. All the exons of the $p^{53}$ gene were amplified by the polymease chain reaction (PCR) using specific oligonucleotide primers. The PCR products were subjected to single-strand conformation polymorphism (SSCP) analysis. A second PCR-SSCP analysis was performed to ensure that the results were reproducible in each experiment, which showed mobility. Levels of DNA methylation were determined.

Results:

TABLE 4

Levels of DNA methylation in normal and cancer cells

| Sample | Mean group incorporation (c.p.m/ng DNA) | Inhibition T/C (%) | P |
| --- | --- | --- | --- |
| Normal gastric cells | — | — | — |
| Gastric cancer cells (no drug) | 2018 ± 232 | — | — |
| Gastric cancer cells treated by Drug | 318 ± 29 | 15.8 ± 1.4 | <0.1 |

TABLE 5

The effect of Drug on $p^{53}$ mutations

| Group | Frequency of $p^{53}$ mutations (%) | Inhibition T/C (%) | P |
|---|---|---|---|
| Normal gastric cells | 0 | 0 | — |
| Gastric cancer cells (no drug) | 35 | — | — |
| Gastric cancer cells treated by Drug | 5 | 14.3 ± 1.5 | <0.01 |

TABLE 6

The effect of Drug on $^{17}p$ allelic loss

| Group | Frequency of $^{17}p$ allelic loss (%) | Inhibition T/C (%) | P |
|---|---|---|---|
| Normal gastric cells | 0 | 0 | — |
| Gastric cancer cells (no drug) | 38 | — | — |
| Gastric cancer cells treated by Drug | 5 | 13.1 ± 1.2 | <0.01 |

A combination of different molecular genetic analysis is a highly sensitive method for analysis of genetic abnormalities. Data of table 3, and 4 showed that Drug can obviously inhibit levels of DNA methylation and $p^{53}$ mutations and $^{17}p$ allelic loss of cancer cells. Table 5 showed that Drug can increase function of tumor suppressor. Molecular genetics has revealed that increased tumor suppressor can treat and prevent cancer.

EXAMPLE 7

The Effect of Drug on Control of Oncogenes

Human myeloblastic leukemic cell (ML-1) had been described previously. Cells were maintained in suspension culture in RPMI 1640 medium supplemented with 7.5% heat-inactivated FBS, Cells growth and viability were assayed by hemocytometer using trypan blue dye exclusion. RNA was isolated by the CsCl gradient modification. RNA pellets were washed twice by reprecipitation in ethanol and quantitated by absorbency at 260 nM. RNA analyzed by electrophoresis of 15 μg of RNA through 1.2% agarose formaldehyde gels followed by northern blot transfer to nitrocellulose.

Single-standard uniformly labeled DNA probes were prepared. Probe of c-myc was a 1.7 Kb cla-Eco RI restriction fragment containing the 3'exon region of human c-myc and probe of c-myb was 1.0 Kb myb-specific Bam HI fragment. Probes for n-ras contained DNA fragments using a modification of the PCR technique. Probes for myb, myc and n-ras were isolated by electrolution. The isolated fragments were labeled to high specific activity with [$\alpha^{32}P$]-dCTP (3000 ci/mmol). Prehybridization of the filter was performed. The hybridization mixer contained 50,000 cpm of probe. The probes were hybridized at 58° C. in 15 mM NaCl, 1.5 nM sodium citrate for 3 hours. After hybridization, they were exposed to XAR-5 film. Oncogene expression was quantitated by densitometer scanning of the autoradiography.

The results are summarized in the tables as below.

TABLE 7

The effect of Drug on inhibition of oncogenes

| Compound (ng/ml) | Inhibition (%) | | | P |
|---|---|---|---|---|
| | c-myb RNA | c-myc RNA | n-ras RNA | |
| Cultured medium | 0 | 0 | 0 | — |
| Saline | 0 | 0 | 0 | — |
| BE(10) | 52.0 ± 5.8 | 50.5 ± 6.1 | 30.2 ± 3.5 | <0.01 |
| BA (10) | 24.4 ± 3.0 | 29.3 ± 3.4 | 20.6 ± 3.0 | <0.01 |
| Drug (10) | 61.8 ± 7.0 | 62.0 ± 7.2 | 38.6 ± 7.5 | <0.01 |

The results presented above clearly suggested that BE and BA has a significant effect of inhibiting oncogenes, and BE plus BA has a synergistic effect.

EXAMPLE 8

Effects of Drug on Tumor Cells Proliferation

Materials and methods:

Hela leukemia HL-60 were routinely cultured in the RPMI1640 medium supplemented 20% fetal calf serum. The experiment was carried out in 96 microplate, each well had $5\times10^5$ cells and given desired concentration of drug (1 μg/ml). Then the plate was incubated at 37° C. in an atmosphere of humidified air enriched with 5 percent carbon dioxide for 72 hours. Inhibition percent rate of tumor cell proliferation was obtained according to the bellow formula.

$$\text{Inhibition percent rate} = \frac{\text{Control} - \text{Test}}{\text{Control}} \times 100\%$$

Results:

Drug inhibited tumor cells growth significantly (Table 8). Percent rates of inhibition were more than 60%.

TABLE 8

Effect of Drug on inhibiting growth cancer cells

| Cell line | Inhibition (%) |
|---|---|
| Control Human cells | — |
| HL-60 | 70.5 ± 8.0 |
| Hela | 63.0 ± 5.1 |

EXAMPLE 9

Drug Inhibited Tumor Incidence in vivo

The capacity of tobacco-specific nitrosamine 4-(methylnitrosamino)-1-(3-pyridyl)-1-butanone (NNK) to induce tumor incidence was recognized several years ago.

Methods:

Every group had 20 mice. For treatment group, each mouse was gave Drug by injection at dose of 20 mg/kg daily. For control group, each mouse was gave same volume of physiological saline.

Three days later, mice were gave 10 μmol NNK (in 0.1 ml saline) by i.p. injection. Sixteen weeks after these treatments the mice were killed and pulmonary adenomas were counted. The statistical significance of bioassay data was determined by student's test.

TABLE 9

Effect of Drug on NNK-induced lung tumorigenesis

| Group | Tumor incidence (%) | P |
| --- | --- | --- |
| Control | 100 | — |
| Drug | 25.0 ± 2.3 | <0.01 |

Data of Table 10 indicated that Drug has a significant inhibitory effect against lung tumor. Drug can decrease tumor incidence. Therefore, Drug can prevent cancer.

The preparation of drugs which can be accomplished by the extraction methods set forth above or any conventional methods for extracting the active principles from the plants. The novelty of the present invention resides in the mixture of the active principles in the specified proportions to produce drugs, and in the preparation of dosage units in pharmaceutically acceptable dosage form. The term "pharmaceutically acceptable dosage form" as used hereinabove includes any suitable vehicle for the administration of medications known in the pharmaceutical art, including, by way of example, capsules, tablets, syrups, elixirs, and solutions for parenteral injection with specified ranges of drugs concentration.

In addition, the present invention provides novel methods for treating and preventing a variety of cancer conditions and control cancer cells with produced safe pharmaceutical agent. It will thus be shown that there are provided compositions and methods which achieve the various objects of the invention and which are well adapted to meet the conditions of practical use. As various possible embodiments might be made of the above invention, and as various changes might be made in the embodiments set forth above, it is to be understood that all matters herein described are to be interpreted as illustrative and not in a limiting sense.

What is claimed as new and desired to be protected by Letter Patent is set forth in the appended claims:

1. A process for producing a pharmaceutical composition of Baicalin, which used for treatment cancer and control cancer cells, comprising:
   a. extracting powder of Scutellaria baicalenisis Georgi or Scutollaria scordifolia Fisch with hot water at 80° C. and allowed to stand a half of hour;
   b. filtering the above mixture and separating a filtrate from residue;
   c. adjusting the pH of the filtrate to 1.5 by HCl;
   d. filtering the above mixture and separating a residue from a filtrate;
   e. the residue was washed by 95% ethanol;
   f. the residue filtered wider vacuum;
   g. distilled water added to residue;
   h. adjusting the pH of the mixture to 6.8 by 40% NaOH;
   i. active carbon added to the solution of NaOH and allowed to stand for a half of hour at 80° C.;
   j. the solution of NaOH allowed to stand 10 hours at room temperature and precipitant was obtained;
   k. the precipitant filtered under vacuum; and
   l. the precipitant was washed by 95% ethanol and dried at 60° C. which composition contains Baicalin.

* * * * *